United States Patent [19]
Phan et al.

[11] Patent Number: 5,674,242
[45] Date of Patent: Oct. 7, 1997

[54] ENDOPROSTHETIC DEVICE WITH THERAPEUTIC COMPOUND

[75] Inventors: Loc Phan, San Jose; Simon Stertzer, Woodside; Michael Froix, Mountain View, all of Calif.

[73] Assignee: Quanam Medical Corporation, Santa Clara, Calif.

[21] Appl. No.: 751,999

[22] Filed: Nov. 15, 1996

Related U.S. Application Data

[63] Continuation-in-part of Ser. No. 486,271, Jun. 6, 1995, Pat. No. 5,603,722.

[51] Int. Cl.⁶ .................................................. A61M 29/00
[52] U.S. Cl. ................................. 606/198; 606/195
[58] Field of Search ........................... 606/198, 195, 606/194; 623/1, 12

[56] References Cited

U.S. PATENT DOCUMENTS

| | | |
|---|---|---|
| 5,108,416 | 4/1992 | Ryan et al. ............................ 623/1 |
| 5,163,952 | 11/1992 | Froix . |
| 5,189,110 | 2/1993 | Ikematu et al. . |
| 5,195,984 | 3/1993 | Schatz . |
| 5,236,447 | 8/1993 | Kubo et al. . |
| 5,336,518 | 8/1994 | Narayanan et al. . |
| 5,370,683 | 12/1994 | Fontaine . |
| 5,441,515 | 8/1995 | Khosravi et al. . |
| 5,441,516 | 8/1995 | Wang et al. . |
| 5,449,372 | 9/1995 | Schmaltz et al. . |
| 5,449,382 | 9/1995 | Dayton . |
| 5,464,650 | 11/1995 | Berg et al. . |
| 5,490,839 | 2/1996 | Wang et al. ............................. 606/194 |

Primary Examiner—Michael Buiz
Assistant Examiner—Kevin Truong
Attorney, Agent, or Firm—Judy M. Mohr; Peter J. Dehlinger

[57] ABSTRACT

An endoprosthetic device for insertion at a vascular site is described. The device is composed of a structural member carrying a polymer member having an embedded therapeutic compound. The polymer member is formed of a shape-memory polymer for expansion upon exposed to a selected stimulus. The structural member is designed for coexpansion with the polymer member when the device is exposed to the stimulus.

17 Claims, 10 Drawing Sheets

ENDOPROSTHETIC DEVICE WITH THERAPEUTIC COMPOUND

The present invention is a continuation-in-part application of U.S. patent application No. 08/486,271, for "Intravascular Stent" filed Jun. 6, 1995 now U.S. Pat. No. 5,603,722.

FIELD OF THE INVENTION

The present invention relates to an endoprosthetic device for insertion in a vessel and for administration of a therapeutic compound.

BACKGROUND OF THE INVENTION

Endoprosthetic devices known as stents are placed or implanted within a vessel for treating problems such as stenoses, strictures, or aneurysms in the vessel. Typically, these devices are implanted in a vessel to reinforce collapsing, partially occluded, weakened or dilated vessels. Stents may also be implanted in the urethra, ureter, bile duct, or any body vessel which has been narrowed or weakened.

Stents made of various materials including metals, alloys and plastics and formed into variety of geometric shapes have been described in the art. Two types of stents have been commonly employed. Spring-like or self-expanding stents, formed typically of metals or alloys, are inserted into the target vessel with a restraining element or sheath over the stent, to prevent the stent from expanding until placement at the target site. The other type of stent requires a stimulus to expand the stent after placement at the target vessel. Most often, this stimulus is radial force or pressure applied by inflation of a balloon on a catheter. Stents which respond to other stimuli, such as heat, are also known, and these stents are generally composed of a shape-memory material, either an alloy or a polymer.

It is often desirable to administer a drug at the target site, where the stent also serves as a framework for carrying the therapeutic compound. Numerous approaches have been proposed and, for metal stents, one proposed approach is to directly coat the stent wires with a polymer containing the therapeutic agent. This approach suffers from several problems including cracking of the polymer as the stent is expanded during deployment. Because the stent wires have a limited surface area, and because the overall polymer coating should be thin so that it will not significantly increase the profile of the stent, the amount of polymer that can be applied is limited. Hence, another disadvantage with polymer-coated stents for drug delivery is a limited capacity for carrying a drug.

Another approach to providing delivery of a drug in combination with a stent has been to include a sheath, which encompasses the stent and contains the therapeutic agent. (Scott U.S. Pat. No. 5,383,928; Martinez, U.S. Pat. No. 5,453,090). Such sheaths are typically secured to the stent by means of a hemostat or other clamping mechanism, which have the disadvantage of increasing the profile of the catheter, reducing flexibility and tractability.

SUMMARY OF THE INVENTION

Accordingly, it is an object of the invention to provide a stent which overcomes the above-mentioned problems.

In one aspect, the invention includes, a drug-delivery endoprosthetic device for insertion at a vessel target site via catheter placement at the site. The device includes a shape-memory polymer member capable of expanding from a contracted state to a stable, radially expanded state when the polymer member is exposed to a selected stimulus. The polymer member has an embedded drug for release from the member when it is placed at the target site. The device also includes a structural member on which the polymer member is carried, and is capable of coexpansion with the polymer member when the device is exposed to the stimulus. The device can be delivered from a catheter, with the structural and polymer members in their contracted states, and is adapted to be held in a vessel at the target site by radial pressure against the wall of the vessel, with the structural and polymer members in their expanded states.

In one embodiment, the polymer member is composed of a shape-memory polymer responsive to a thermal stimulus at a temperature between about 25°–100° C.

The polymer member is coextensive with the structural member, or, in other embodiments, the polymer member encases the structural member and, in its contracted state, is effective to restrain the structural member in its contracted state.

In one embodiment, the thermally-responsive polymer member is formed of a memory polymer having a thermally-activated polymer-state transition which is a melting point of the polymer; a glass-transition of the polymer; a liquid crystal transition; or a local mode molecular transition. Such a polymer can be an acrylate-containing or a methacrylate-containing polymer.

In another embodiment, the structural member expands in response to a heat stimulus or radial force. Preferably, such a structural member composed of a metal or alloy such as Nitinol, stainless steel, titanium, tantalum, cobalt, platinum, and iridium.

In a preferred embodiment, the structural member is composed of a shape-memory alloy for radial expansion at a critical temperature by activating a heat-recoverable memory diameter and the device is heated to the critical temperature. In another preferred embodiment, the structural member is composed of a heat-activated, shape memory polymer. In another preferred embodiment, the structural member is composed of a metal and designed for self-expansion.

The drug embedded in the polymer member is, for example, an anticoagulant, an antiproliferative agent, a vasodilator, a nitrate, an antioxidant, antisense oligonucleotide, an antiplatlet agent, or a clot dissolving enzyme. In a preferred embodiment, the drug is the anticoagulant heparin.

In one embodiment, the polymer member is carried on the structural member and is secured thereon by an adhesive. The adhesive can be, for example, a biopolymer, such as a protein or a peptide. The adhesive can also be prepared from a synthetic polymer which swells or is soluble in water, and exemplary polymers are given below. In a preferred embodiment, the adhesive is prepared from heparin.

These and other objects and features of the invention will be more fully appreciated when the following detailed description of the invention is read in conjunction with the accompanying drawings.

DETAILED DESCRIPTION OF THE INVENTION

The endoprosthetic device of the present invention, also referred to herein as a stent, is designed for insertion at a vessel target site via a catheter. As will be described, the low-profile, self-restraining stent is designed for expansion in response to a stimulus and for administration of a therapeutic compound for release at the target site.

In its most broad aspect, the device is composed of a structural member and a polymer member. The two members are designed for coexpansion, where, in one embodiment, the members are coextensive and, in another embodiment, the polymer member encases the structural member. Each of these embodiments will be described below in detail.

Figure 1A:
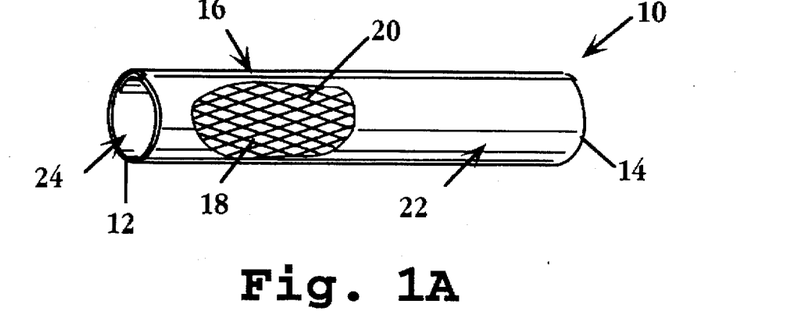
FIGS. 1A–1D illustrate an endoprosthetic device in accordance with one embodiment of the invention, where the structural member is encased by the polymer member, and where the device is shown in a contracted, predeployed state (FIG. 1A) and in an expanded state in side view (FIG. 1B), in an end view (FIG. 1C) and in cross section (FIG. 1D)
Figure 1B:
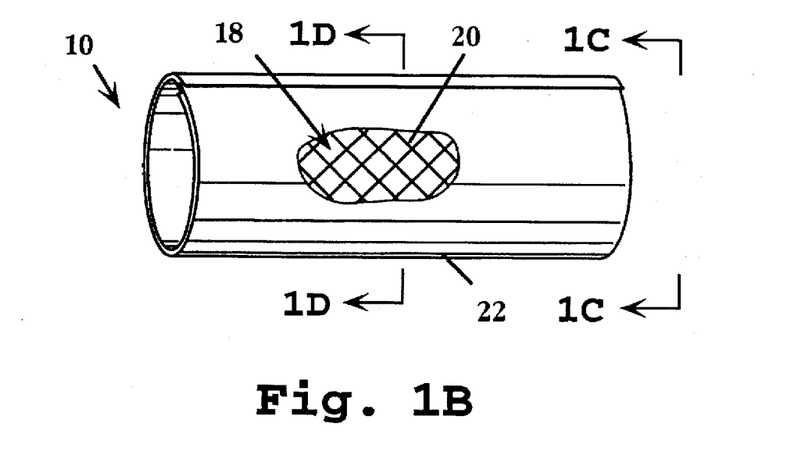
Figure 1C:
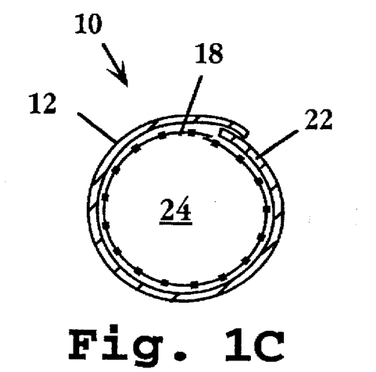
Figure 1D:
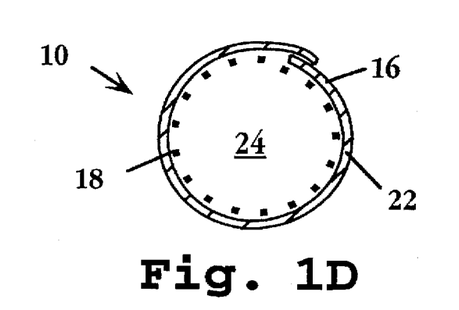

A first embodiment of the device is shown in FIGS. 1A–1D, where the structural member is encased by the polymer member. Seen in FIG. 1A is a device 10 shown in a contracted state for insertion into a vessel via a catheter for placement at a target site, as will be described. The device is generally tubular or cylindrical in shape, and has first and second ends 12, 14 and an external surface 16 therebetween. A structural member 18 gives mechanical strength to the device and, importantly, carries on its outer surface 20 a polymer member 22. In accordance with this first embodiment shown in FIG. 1, the polymer member encases or surrounds the structural member. In FIGS. 1A–1B, a portion of the polymer member has been cut away to expose the outer surface 20 of the structural member for purposes of illustration.

Polymer member 22 is carried on the structural member and is secured thereon, by the self-restraining nature of the member or by a suitable adhesive, as will be described below. Ends 12, 14 of stent 10 are unobstructed by the polymer member, as seen best in the end view of FIG. 1C, to allow for fluid flow through a central opening 24 of the device.

FIG. 1B shows the device in its expanded state, achieved by coexpansion of the polymer member and the structural member in response to at least one stimulus. As will be described below in more detail, the device is expanded by, for example, exposing the members to a heat stimulus to activate a material transition for recovery to a memory state or by a radial force, such as provided by inflation of a balloon on a catheter.

Figure 2A:
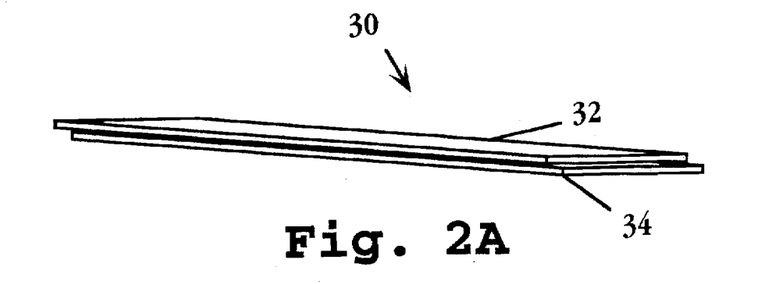
FIGS. 2A–2D illustrate an endoprosthetic device in accordance with a second embodiment where the device members are coextensive, the device is shown in its memory condition (FIG. 2A), a contracted condition (FIG. 2B), an expanded condition (FIG. 2C) and in an end view (FIG. 2D)
Figure 5A:
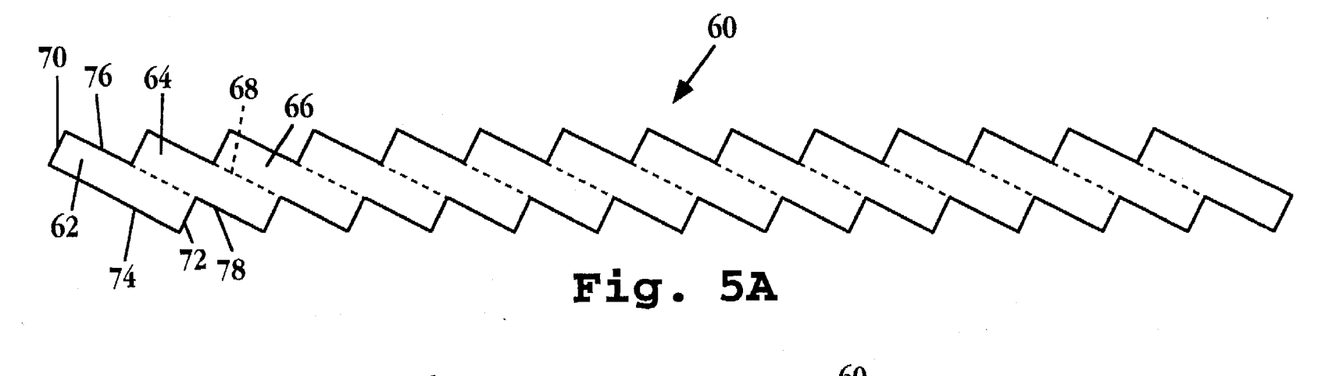
FIGS. 5A–5C show a geometric configuration for one or both members of the device of the invention, where the member is shown in a memory state (FIG. 5A), a contracted state (FIG. 5B) and in an expanded state (FIG. 5C)
Figures 5B, 5C:
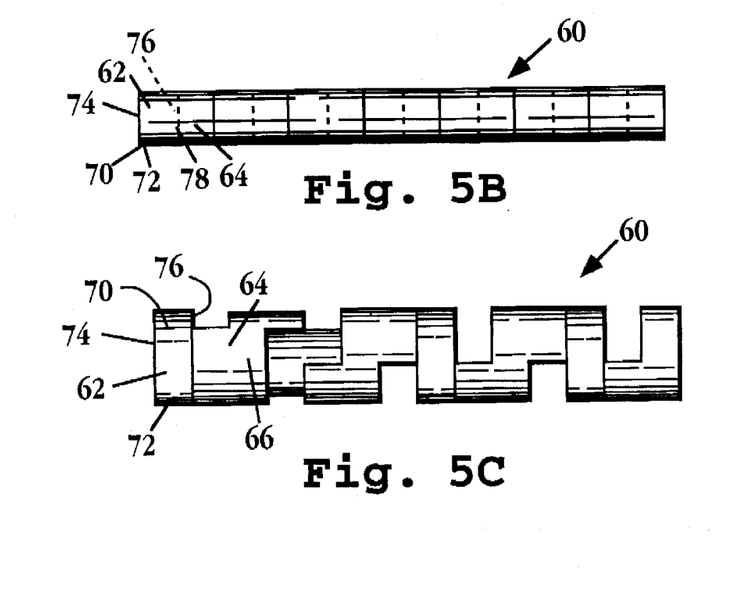
Figure 6A:
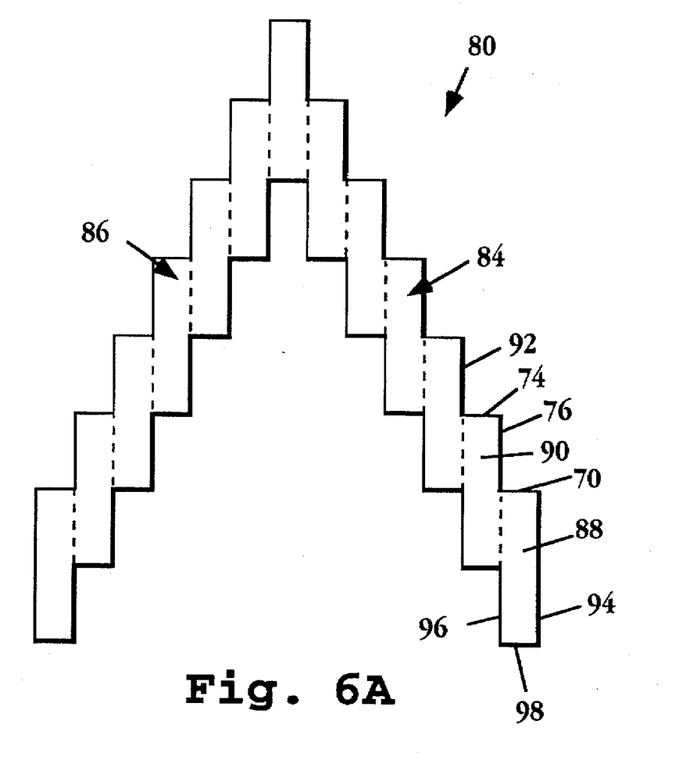
FIGS. 6A–6C show another geometric configuration for one or both members of the device of the invention, where the member is shown in a memory state (FIG. 6A), a contracted state (FIG. 6B) and in an expanded state (FIG. 6C)
Figure 6B:
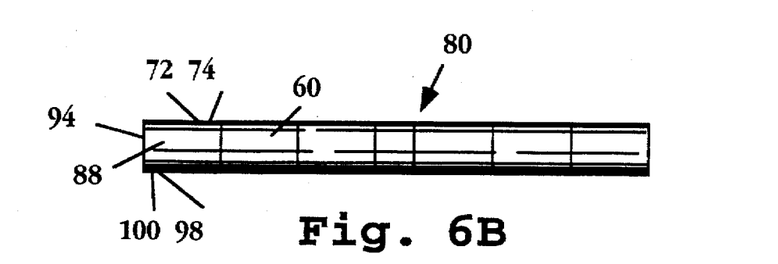
Figure 6C:
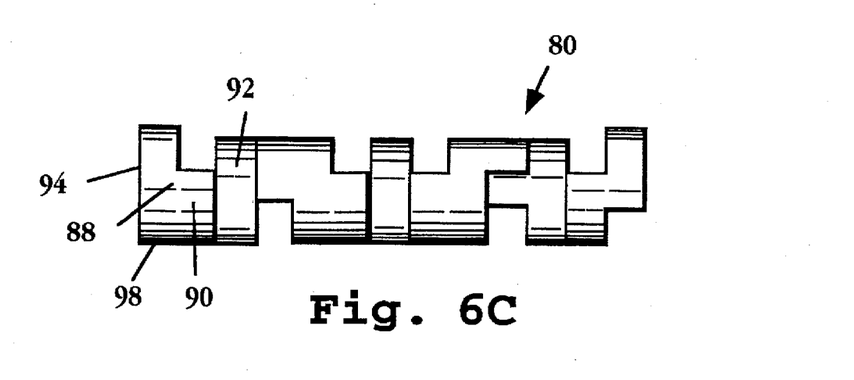

A second embodiment of the device is shown in FIGS. 2A–2D, in which the polymer member is coextensive with the structural member. With reference to FIG. 2A, an endoprosthetic device 30 composed of a shape-memory polymer member 32 and a structural member 34 is shown. In this embodiment, the members are each composed of a shape-memory material, for example, the structural member is composed of a shape-memory alloy and the polymer member is composed of a shape-memory polymer. In FIG. 2A, the members are shown in their memory states, that is, the condition to which the members return upon activation by exposure to a suitable stimulus. The configuration or geometry of the members can be widely varied from the parallelogram shown in FIG. 2A, to other configurations, such as shown in FIGS. 5–6, discussed below. While the geometries of the polymer member and the structural member shown in FIG. 2 are the same, it will be appreciated that the geometries of the two members can be different.

Importantly, in the embodiment shown in FIG. 2, the structural member and the polymer member are coextensive —that is, the members extend together along parallel planes. In a preferred embodiment, the members are both formed of a shape-memory material and are placed into a coextensive, small-diameter, contacted state, shown in FIG. 2B, by activating the material transition, e.g., warming the shape-memory material to above its critical temperature, and winding the members together around a balloon catheter. The members are cooled below their critical temperatures to secure the device in its small-diameter, contracted configuration.

Figure 2B:
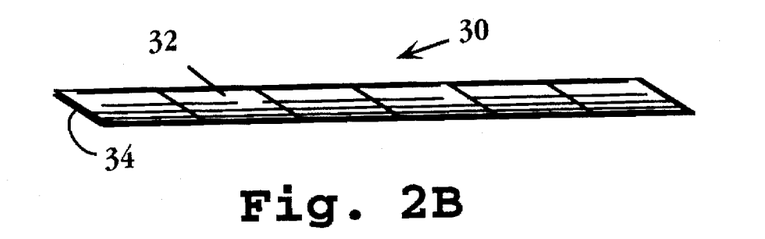
Figure 2C:
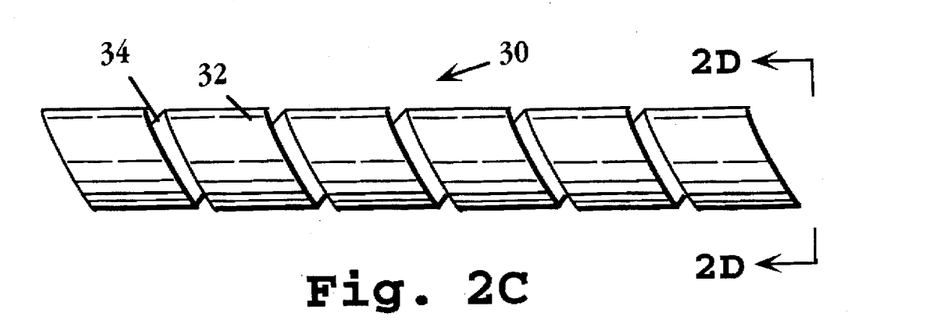
Figure 2D:
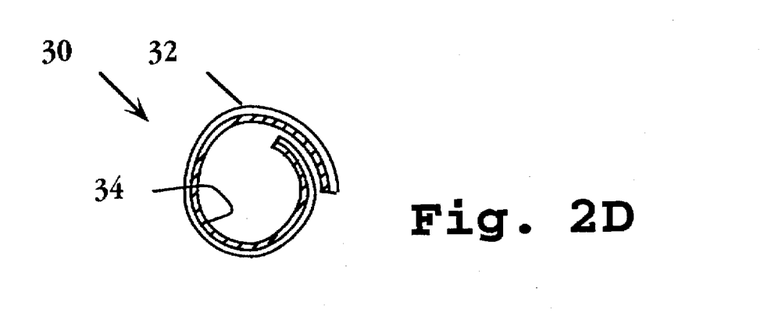

Upon activation of the material transition, the coextensive members coexpand toward their memory conditions, to a larger-diameter state, as shown in FIG. 2C. It will be appreciated that the members expand toward the memory state shown in FIG. 2A, however, when the device is placed in a target vessel, expansion of the members is constrained by the walls of the vessel.

As shown in FIG. 2, polymer member 32 is disposed on the outer surface of the endoprosthetic device, with the structural member on the inside. This arrangement is preferred in a device where the structural member is composed of a non-shape memory material or where the structural member is self-expanding. The polymer member, being formed of a shape-memory polymer, is self-restraining in its contracted state and serves to restrain the structural member as well. When the polymer member is activated for expansion, the structural member coexpands by virtue of its self-expanding design or in response to a stimulus, such as radial force from inflation of a balloon catheter.

However, it will be appreciated that the arrangement of members can be reversed, to place the structural member on the outside of the device. Placement of the polymer member on the inner surface of the device is desirable in cases where the polymer member is less thrombogenic than the structural member.

A. The Structural Member

The structural member of the device is formed preferably of a metal or an alloy, including shape-memory alloys. Exemplary metals include stainless steel, titanium, nickel, tantalum, cobalt, platinum and iridium. Exemplary alloys include alloys of these metals, Cu-Zn-Al, Cu-Al-Ni and shape-memory alloys of Ni-Ti alloys, known under the name Nitinol, Bimetal or Memotal.

The structural member of the device may also be formed from a polymer, in particular a shape-memory polymer, and exemplary polymers are given below.

The structural member can take a wide variety of geometries or configurations, such as those described herein, and those known in the art. Commercially available stents suitable for use as the structural member include Johnson & Johnson's Interventional Stent System, a low-profile stent from Arterial Vascular Engineering and the Cook Stent, from Cook Cardiology Co.

B. The Polymer Member

The polymer member of the device is formed from a shape-memory polymer formulated to have a polymer-state transition that responds to a selected stimulus. Upon exposure to the stimulus, the polymer transition is activated and the polymer member moves from a contracted, small-diameter state to an expanded, larger-diameter state, as described above with respect to FIG. 2.

Shape-memory polymers suitable for use in the present invention include, for example, those described in U.S. Pat. No. 5,163,952, which is incorporated by reference herein. In particular, the shape-memory polymer is a methacrylate-containing or an acrylate-containing polymer, and exemplary formulations are given below.

As discussed above, the shape-memory polymer member is characterized in that it will attempt to assume a memory condition in response to a stimulus which activates a polymer transition. Such a stimulus can be (i) adsorption of heat by the polymer, (ii) adsorption of liquid by the polymer, or (iii) a change in pH in the liquid in contact with the polymer.

Polymers responsive to heat are those that undergo a thermal transition at a critical temperature. For example, such a thermal transition can be a crystalline melting point of the either the main chain or a side chain of the polymer, preferably between about 25°–100° C.; a glass-transition at a temperature of between 25°–100° C., more preferably between 25°–80° C.; a liquid-crystal phase (mystifies) temperature transition; or a local mode molecular transition.

Polymers responsive to adsorption of a liquid are formulated by incorporating in the polymer a hydrophilic material, such a n-vinyl pyrrolidone. Typically, upon exposure to an aqueous medium the n-vinyl pyrrolidone absorbs water and swells, causing expansion of the polymer.

Polymers responsive to a change in pH are formulated by incorporating pH sensitive materials into the polymer, such as methacrylic acid or acrylic acid. Typically, these polymers swell in response to a change in ionic environment, for movement between a small, contracted state and a larger, expanded state.

In a preferred embodiment of the invention, the polymer member is prepared from a polymer that is sensitive to heat. Typically, these polymers are thermoplastic polymers which soften and take on a new shape by the application of heat and/or pressure. These polymers can be crosslinked to varying degrees so that the polymer will soften with heat but not flow.

As discussed above, preferably, the shape-memory polymer for use in forming the structural member of the device is a heat-sensitive, polymer, and in particular a methacrylate-containing or an acrylate-containing polymer.

An exemplary methacrylate-containing memory polymer is prepared by mixing the monomers methyl methacrylate, polyethyleneglycol methacrylate, butylmethacrylate in a 2:1.5:1 ratio. A crosslinker, such as hexanedioldimethacrylate, and a thermal or UV initiator, such as benzoin methyl ether or azobisisobutylnitrile (AIBN). The monomers can be polymerized into a polymer for extrusion in a conventional extruder to provide a length of a tubular structure or a flat sheet, which are cross-linked by exposure to UV light, high energy electrons, gamma radiation or heat. The monomers can also be polymerized in a transparent spinning tube to form a tubular structure.

In experiments performed in support of the present invention, described below, polymer members were formed from the monomers methyl methacrylate, polyethyleneglycol methacrylate, and butylmethacrylate. The monomers were crosslinked using hexanedioldimethacrylate and the polymerization was initiated using Darocur, as will be described in Examples 1–4.

Mother exemplary thermoplastic polymer is polyethylene oxide, a heterochain thermoplastic with a crystalline melting point around 65° C. Polyethylene oxide can be crosslinked using a multifunctional acrylate or methacrylate, such as triallylisocyanurate. Thermoplastic blends are also suitable memory polymers, such as blends of polyethylene oxide with methylmethacrylate, polyethylene, polycaprolactone, or trans-polyoctenamer (Vestenamer®). Typically, between 10–90%, preferably 30–70%, of polyethylene oxide is present in the blends. The blends can be crosslinked using conventional multifunctional crosslinkers.

Other preferred polymers are those prepared by condensation polymerization and free radical, or addition, polymerization. Condensation polymers are those in which the molecular formula of the repeat unit of the polymer chain lacks certain atoms present in the monomer from which it was formed, or to which it can be degraded. Exemplary condensation polymers include polyester, polyanhydride, polyamide, polyurethane, cellulose, polysiloxane.

Radical chain, or addition polymers are those in which a loss of a small molecule does not take place, as in condensation polymers. Polymers formed by addition polymerization include polyethylene, polymethyl methacrylate, polyvinyl chloride, and polyacrylonitrile.

C. Therapeutic Agent

The endoprosthetic device of the invention includes a therapeutic agent embedded in the polymer member for release at the target site. The drug is incorporated into the polymer member by passive diffusion after fabrication of the member, or more preferably, by addition of the drug to the polymer prior to extrusion of the polymer member or prior to polymerization of the member.

Exemplary drugs include heparin to prevent thrombus formation; an antiproliferative agent, such as methotrexate; a vasodilator, such as a calcium channel blocker; a nitrate; antiplatlet agents, such as ticlopidine, abciximab (ReoPro™), Integrelin™; clot dissolving enzymes, such as tissue plasminogen activator; antisense oligonucleotides; urokinase; streptokinase; antioxidants, such as vitamin E and glutathione; finasteride (Proscar®) for treatment of benign prostatic hyperplasia; estrogen-mediated inhibitors of neointima formation; nitric oxide releasing compounds, such as n'-dimethylhexane diamine and 1-arginines; virus-mediated gene transfer agents; antimitogenic factors and antiendothelin agents.

In experiments performed in support of the present invention, polymer members containing various therapeutic agents were prepared and in vitro release rates were measured. Polymer members containing ticlopidine, in neat form and in encapsulated form (Examples 5 and 6), vitamin E (Example 7), antisense oligonucleotide (Example 8), glutathione (Example 9), and heparin (Example 10) were prepared.

D. Device Configurations

The structural and polymer members of the device can take any number of geometric configurations, and exemplary configurations, in addition to those discussed above in FIGS. 1 and 2, are illustrated in FIGS. 3–6.

Figure 3A:
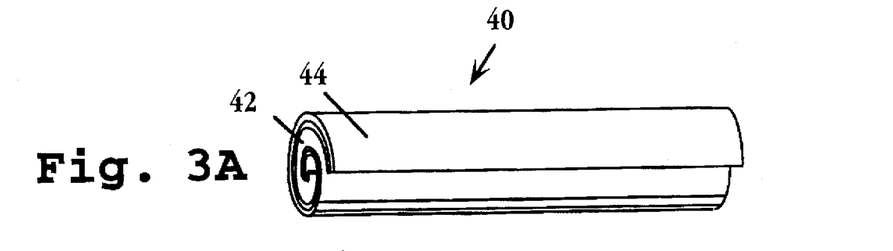
FIGS. 3A–3B illustrate another device configuration where the members are coextensive, where the device is shown in a contracted, predeployed state (FIG. 3A) and in an expanded state (FIG. 3B)
Figure 3B:
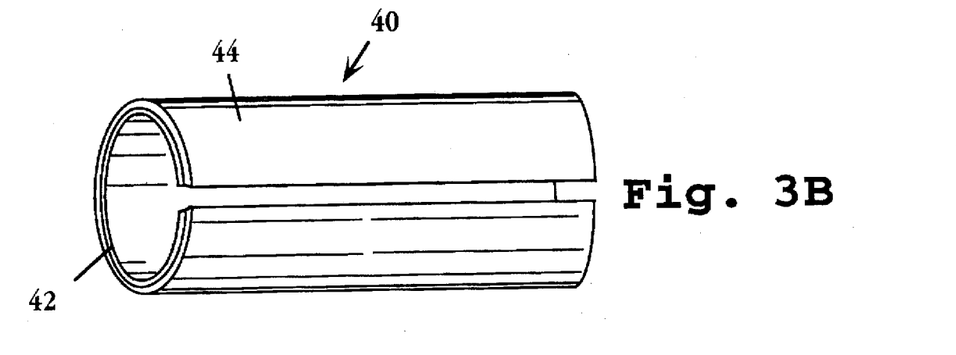

FIGS. 3A–3B show an endoprosthetic device 40 having a structural member 42 and a coextensive polymer member 44. Polymer member 44 has an embedded drug and is carried on the outer surface of the structural member. The members have a flat sheet configuration and form a device, which in the contracted state (FIG. 3A) is spiraled into a small-diameter cylinder.

The structural member in the device of FIG. 3 is a self-expanding stent, where the structural member in its contracted state is under tension and in the absence of a restraining member, will expand to its larger diameter state, shown in FIG. 3B. The polymer member acts as a restraining member for the structural member. The polymer member, formed of a shape-memory polymer, is self-restraining, e.g., it maintains its small-diameter condition until the polymer transition is activated. This feature of the device is beneficial in maintaining a low device profile.

Expansion of the device is achieved by exposing the polymer member to a stimulus, such as heat, to activate the polymer transition. As the polymer member expands, the structural member is no longer restrained and coexpands with the polymer member.

It will be appreciated that the device shown in FIG. 3A–3B can be formed of a variety of materials and geometries. For example, the structural member can be either a polymer or a metal and the flat sheet configuration may be provided with slots, openings or gaps. It will further be appreciated that the structural member and the polymer members can have different geometries.

Figure 4A:
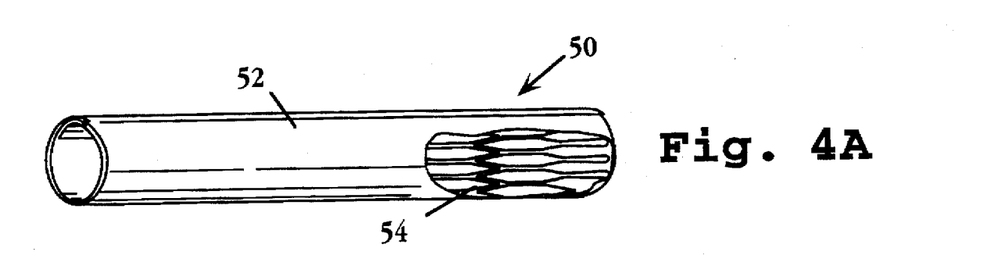
FIGS. 4A–4C illustrate another device configuration where the polymer member encases the structural member, the device being shown in a contracted, predeployed state (FIG. 4A) and in an expanded state (FIG. 4B) and in and end view (FIG. 4C)
Figures 4B, 4C:
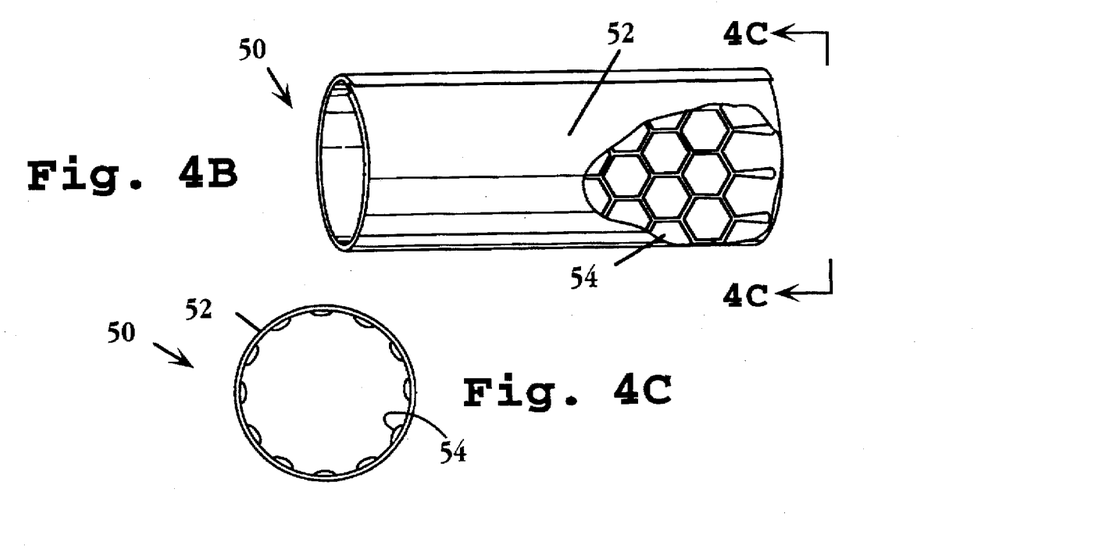

FIGS. 4A–4C illustrate another device configuration, where an endoprosthetic device 50 includes a polymer member 52 encasing a structural member 54. In this configuration, the structural member is preferably formed of a shape-memory alloy, such as Nitinol. The polymer member, as in the above-described configurations, is composed of a shape-memory polymer. Each member is responsive to a thermal stimulus at a critical temperature, and preferably, the critical temperatures of each member are within a few degrees. In this way, the device is expanded by filling the balloon of a catheter with a warm fluid to expand both the structural and polymer members of the device.

FIGS. 5 and 6 illustrate other possible geometries for the stent members. FIG. 5A shows a linear, unitary strip 60 formed of a series of expandable segments, such as segments 62, 64, 66. The dashed lines in the figure, such as line 68, are drawn to aid in visualizing the strip segments. Segment 62, which is representative, is defined by ends 70, 72 and sides 74, 76.

The segments are joined along offsetting side regions, that is, segments 62 and 64 are joined along sides 76 and 78. The device is taken from its memory condition shown in FIG. 5A to a small-diameter contracted state of FIG. 5B by winding the strip segments around a balloon catheter. Where the strip is the polymer member of the device and is formed of a shape-memory polymer, the strip is exposed to a stimulus, e.g., heated to or just above its glass-transition temperature, to soften the strip into a more flexible state. Where the strip is the structural member of the device and not a shape-memory material, a metal strap of the same geometric is placed coextensive with the polymer member for winding. After winding the polymer member is cooled to below its transition to retain the member in its small-diameter, contacted state, as shown in FIG. 5B.

FIG. 5C shows stent 60 in its expanded condition, after exposure to a selected stimulus, as discussed above, such as heat. For example, warm saline or other appropriate liquid in a temperature range of 25°–100° C., more preferably 40°–100° C., is introduced into the balloon of the catheter. Heat is transferred from the liquid to the polymer stent, and at a selected temperature the polymer undergoes a thermal transition where the stent segments become flexible and begin to move toward their memory condition. The segments expand until movement is constrained by the walls of the vessel, placing the stent in its open, expanded-diameter, condition.

FIGS. 6A–6C show another geometric configuration for one or both members of the device of the invention, where the members take the form of a v-shaped unitary strip. As seen in FIG. 6A, a v-shaped unitary strip 80 has two portions or legs 84, 86, each formed of a plurality of segments, such as segments 88, 90, 92. Segment 88, which is representative, is defined by sides 94, 96 and ends 98, 100. Strip 80 is shown in FIG. 2A in its memory condition as a flat strip, and is placed in its closed, contracted condition shown in FIG. 2B, by exposing the strip to a stimulus, as discussed above, to activate a polymer transition. For example, the polymer segments can be heated to their glass transition temperature or to their crystalline melting point. The heated strip segments are wound around a balloon catheter and cooled below the transition temperature to secure the segments in their closed conditions. FIG. 6C shows the stent in an expanded state after exposure to a selected stimulus.

In the above-described embodiments, the polymer member is carried on the structural, both where the polymer member encases the structural member and where the polymer member is coextensive with the structural member. Typically, the polymer member is composed of a shape-memory polymer which is self-restraining. That is, the polymer member is retained on the structural by virtue of its being in its small-diameter, contracted state. In the embodiment where the polymer member encases the structural member, the contracted state of the small-diameter serves, in some cases, to act as a restraining member for the structural member, as described above.

E. Device Preparation

In preparing the endoprosthetic device of the present invention, the polymer member and the structural members are each prepared and then brought together to form the device. The selection of material for each of the device members depends in part of the configuration of each member and on whether the polymer member encases the structural member or is coextensive with the structural member.

Example 1 describes preparation of endoprosthetic device where the structural member and the polymer members are coextensive. The polymer member is prepared from a monomer mixture that is polymerized by exposure to UV light. The resulting polymer film has a thermal transition between about 35°–50° C. and a polymer member is cut, using a precision blade or a laser, to the desired geometry. The polymer member is placed in its small-diameter, contracted state by heating the member above its thermal transition and wrapping the member around an appropriate sized tube or rod. The member is cooled to set the shape and removed from the tube. The member is then slipped over a structural member, typically a metal or metal alloy stent purchased from commercially available sources or prepared according to known methods. For example, the Johnson & Johnson Interventional System Stent, having a slotted tube design, can be used, as can a Cook Stent, from Cook Cardiology. It will be appreciated that the polymer member can be wrapped directly around the structural member rather than around a rod or tube.

Example 2 describes preparation of a device where the structural member is encased by the polymer member. The polymer member is prepared from a polymer mixture which is heated and blended in a conventional extruder for extrusion to the desired geometry, either a cylindrical tube or a rectangular strip. In the Example, the polymer member is prepared from polyoctenylene and polyethylene glycol and crosslinked with triallyl isocyanurate. Other polymers, such as polyethylene, are also suitable.

After extrusion, the polymer member is cut the appropriate length and slipped over the structural member or cowound with the structural member, depending on the geometry of each member. For example, a structural member having a flat rectangular shape can be prepared from Nitinol, available from Shape Memory Applications (Santa Clara, Calif.).

The structural member and the polymer member, having the same geometry are heated to above their respective transition temperatures and cowound around a stainless steel rod, having a diameter selected according to the desired final stent size. The members are cooled while being restrained in the contracted shape around the rod, to form the device.

In the case where the structural member and the polymer member of the device are both formed of a polymer, the device may also include a radio-opaque material, such as gold, stainless steel, platinum, tantalum, bismuth, metal salts, such as barium sulfate, or iodine containing agents, such as OmniPaque® (Sanofi Winthrop Pharmaceuticals). The radio-opaque material may be incorporated into the polymer prior to extrusion of device members, or a radio-opaque coating may be applied to one or both of the members. The radio-opaque material provides a means for identifying the location of the stent by x-rays or other imaging techniques during or after stent placement. Preparation of a polymer member having regions of radio-opacity, provided by gold particles dispersed in the polymer member, is described in Example 3.

An endoprosthetic device was prepared using a polymer member including a radio-opaque material, as described in Example 3D. The polymer member was mounted on a stent from Arterial Vascular Engineering, which served as the structural member of the device, and tested for optical density. The device having the radio-opaque polymer member had a greater optical density than the structural member alone.

In another embodiment, the polymer member is carried on the structural member and is secured thereon by an adhesive. The adhesive can be used to secure the polymer member to the structural member or to maintain the polymer member in its small-diameter, contracted state, e.g., the adhesive is applied to the polymer member only. An example of the former case is described in Example 4, where an endoprosthetic device having a polymer member adhesively secured to the structural member is prepared.

The adhesive is prepared from either a synthetic polymer material, a natural polymer or a biopolymer. Synthetic polymer materials for use in preparing the adhesive are those polymers which swell or are soluble in water. Exemplary water-soluble or water-swellable polymers include polyvinyl alcohol, polyvinyl pyrrilodone, polyethylene oxide, celluloses, such as hydroxypropyl cellulose, polyacrylic acid, polymethacrylic acid, and polycyanoacrylates. Naturally occurring materials suitable for use as an adhesive include collagen, fibrin, gelatin, polylysine, polysaccharides, glycoproteins and heparin. The adhesive can also be prepared from a biopolymer, such as a protein or a peptide. Preferably, the adhesive swells or dissolves in the presence of water. In this way, adhesive in an endoprosthetic device placed at a target site, takes on water from the surrounding tissues and weakens, to allow for expansion of the device.

The size, diameter and length, of the endoprosthetic device is tailored to each specific application. For example, for cardiovascular applications, the device can have a length ranging from 0.5 cm to approximately 3 cm. The diameter of the device in its expanded state can range from 0.1 mm to 5 cm, depending on the inner diameter of the target vessel. Small body vessels, such as a intracranial vessel, have an inner diameter of about 0.1 mm. Larger body vessels, such as the aorta, are around 0.5–5 cm in diameter, depending on the size of the individual. The expansion ratio of the device, that is the ratio of the device's outer diameter in the expanded state to the outer diameter in the contracted state is between about 2 and 2,000, depending on several parameters, such as the composition and geometry of the polymer and structural members.

As discussed above, the polymer member contains a therapeutic agent for release at the target site. Preparation of polymer members formed of a heat-sensitive methacrylate-based polymer and containing various drugs are described in Examples 5–10.

Figure 7A:
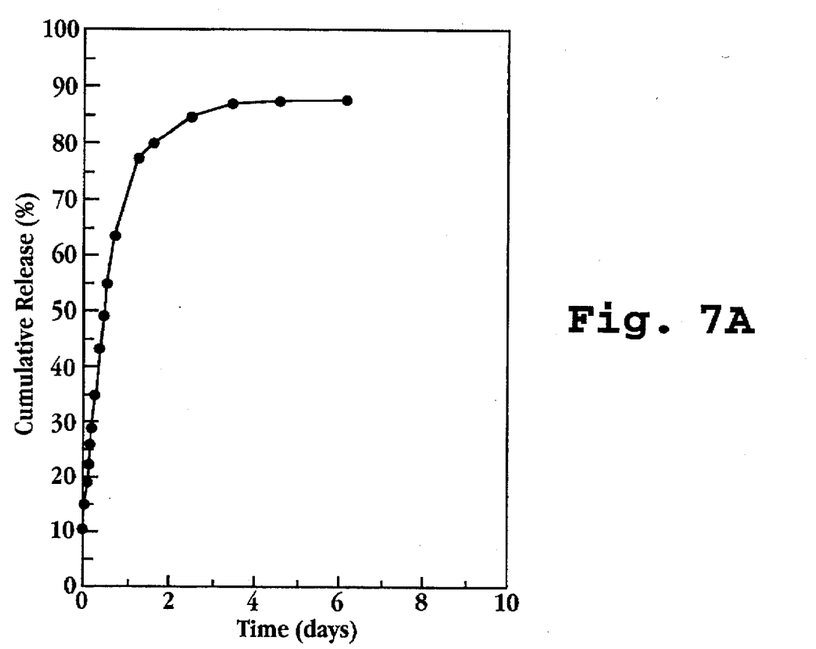
FIGS. 7A–7B are plots showing in vitro cumulative release of ticlopidine from a polymer member as a function of time, in days, where ticlopidine was incorporated into the polymer member in neat form (FIG. 7A) and in microencapsulated form (FIG. 7B)
Figure 7B:
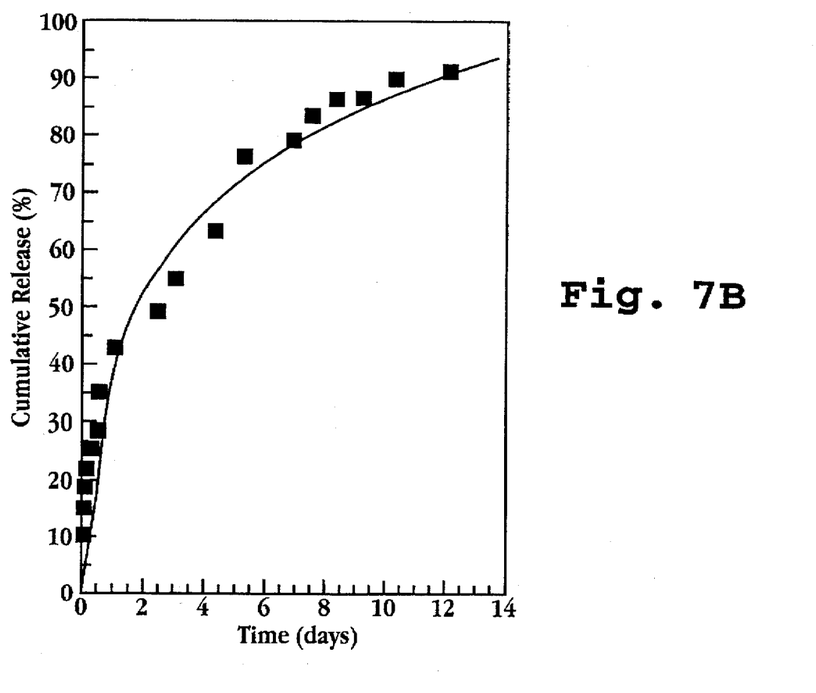

Examples 5 and 6 describe preparation of a polymer member containing ticlopidine in neat form (Example 5) and in entrapped in microcapsules (Example 6). In vitro release of ticlopidine from the polymer members was measured, and the results are shown in FIGS. 7A–7B. FIG. 7A shows cumulative release of ticlopidine as a function of days, and, as seen, 85% of the drug load was released after about 4 days. Encapsulating the drug in polylactide/glycolide-based microcapsules effectively slowed the release of ticlopidine from the polymer member, releasing 85% of the drug in about 10 days, as shown in FIG. 7B.

Preparation of polymer members containing vitamin E, antisense-oligonucleotide, glutathione and heparin are described in Examples 8–10, with in vitro release rates are shown in FIGS. 8–11A, respectively. In vivo release of heparin from the polymer member prepared in Example 10 and implanted into a dog is shown in FIG. 11B.

F. Method of Use

Figure 12A:
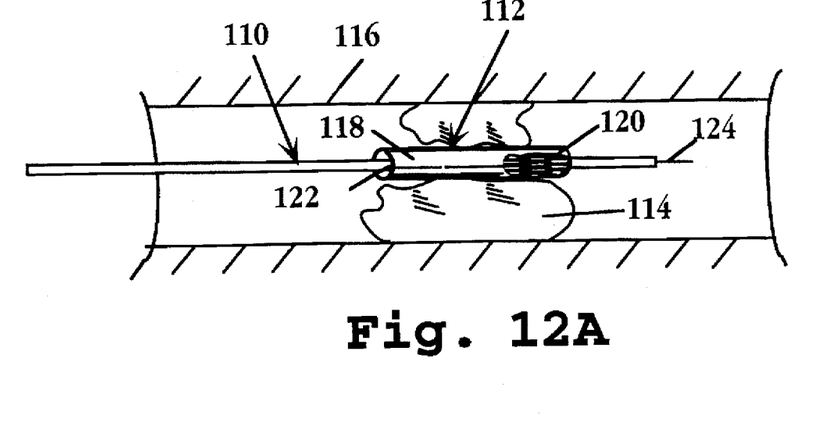
FIGS. 12A–12C show a method for inserting the endoprosthetic device in a vessel via catheter placement, where the device is fitted snugly around a balloon catheter (FIG. 12A), the device is stimulated for expansion (FIG. 12B) and the catheter is withdrawn, leaving the stent in its expanded condition pressing against the sides of the target vessel (FIG. 12C).
Figure 12B:
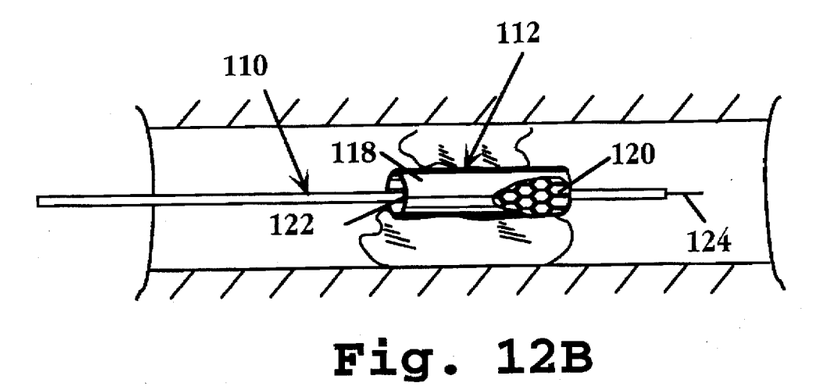
Figure 12C:
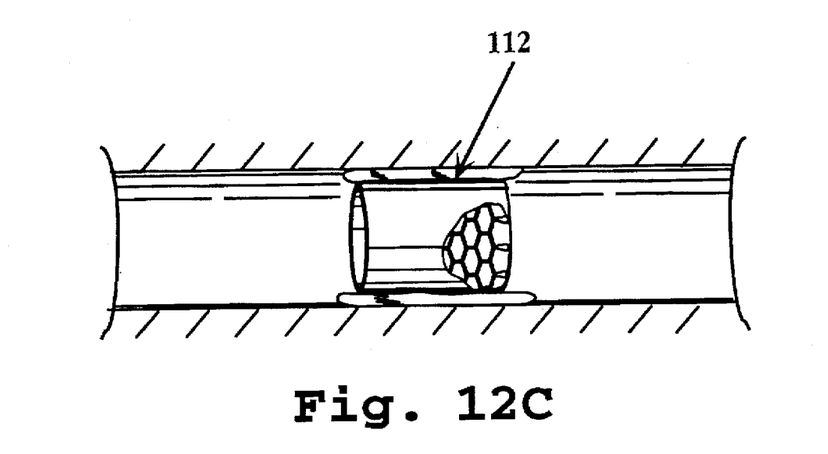

As discussed above, the endoprosthetic device of the present invention is placed at a target vascular site by a transluminal angioplasty catheter. Placement of a device by this method is illustrated in FIGS. 12A–12C. As seen in FIG. 12A, a balloon catheter 110 is used to deliver a stent 112 to a target site 114 in a vessel 116. Stent 112 is like that described with respect to FIG. 1, where the stent is composed of a structural member 118 having a wire-mesh configuration, and a polymer member 120 encasing the structural member. A portion of polymer member 120 is cut away to expose structural member 118 for purposes of illustration. Polymer member, as described above, is formed of a shape-memory polymer having a therapeutic drug embedded in the polymer. In FIG. 12A, the device takes the form of a flexible, cylindrical sleeve that is carried, with each member in its small-diameter, contracted state, on the uninflated balloon 122 of catheter 110. The catheter is introduced over a conventional guidewire 124 and the stent is positioned within the target site using, for example, fluoroscopic imaging.

Once the stent is properly positioned, balloon 122 is filled with a liquid to stimulate the polymer-state transition of the polymer member. As discussed above, the polymer transition may be thermally induced or may be activated by a change in pH or adsorption of a liquid. Upon exposure to the stimulus, the stent expands from its small-diameter state toward its memory condition. For example, a stent having a thermally-activated polymer transition is stimulated to expand by filling the catheter balloon with a heated liquid, such as a contrast agent heated to between about 40°–100° C. Heat from the liquid is adsorbed by the polymer member. The catheter itself may be specifically designed for injection of a heated liquid and for better heat transfer. For example, the catheter may have a double lumen for recirculation of the heated liquid in the balloon region of the catheter.

The stimulus may also be a pH stimulus or a liquid stimulus, where a buffer solution of a selected pH is introduced into the balloon. Small openings in the balloon, introduced prior to placement of the stent around the balloon, would allow the liquid to contact the stent.

In a preferred embodiment, the stimulus is a thermal stimulus, and a heated liquid is introduced into the balloon. Heat from the liquid is conducted convectively to the polymer stent, raising the temperature of the stent to its thermal transition, such as a glass transition temperature of between about 25°–100° C., more preferably between 25°–80° C., and most preferably between 35°–70° C. As illustrated in FIG. 12B, the polymer member responds to the stimulus by moving toward its memory condition. The structural member coexpands with the polymer member, either in response to the thermal stimulus, the radial force of the inflated balloon or by the self-expanding design of the structural member. Expansion of the device continues until the members are constrained by the vessel walls, as illustrated in FIG. 12C. Once the stent is fully deployed with the segments in their expanded condition, the catheter may be withdrawn over the guidewire, and the guidewire removed.

EXAMPLES

The following examples detail preparation of endoprosthetic devices in accordance with the invention and are intended to be exemplary and in no way to limit the scope of the invention.

Example 1

Endoprosthetic Device Having Coextensive Structural and Polymer Members

A. Preparation of Polymer Member

The polymer member is prepared using the materials indicated in Table 1.

TABLE 1

| Material | wt % |
| --- | --- |
| polyethyleneglycol (1000) methacrylate (NOF Corp.) | 33 |
| methylmethacrylate (Aldrich) | 47 |
| butyl methacrylate (Rhom Tech Inc) | 14 |
| hexanedioldimethacrylate (Aldrich) | 5 |
| Darocur 1173 (Ciba-Geigy) or azobisisobutylnitrile (AIBN, Aldrich) | 1 |

The materials in Table 1 are mixed together in the specified amounts, purged with nitrogen, and then polymerized between glass plates to form thin films having a thickness of approximately 0.14 mm. The film is cut into parallelogram strips and any unpolymerized monomer is removed by solvent extraction. The polymer member is formed into its small-diameter, contracted state by heating the polymer above its transition temperature, wrapping it around a small stainless steel rod and cooling it to room temperature while restraining it on the rod, with a snug-fitting section of tubing.

B. Device Preparation

An endoprosthetic device is prepared using the polymer member prepared in Example 1A. The structural member was a commercially available stent from Johnson & Johnson, having a slotted tube design. The polymer member is slipped over the structural member and secured around the structural member by heating the device above the polymer member's transition temperature and cooling the device to room temperature while restraining it with a snugly fitting tube. The tubing is removed prior to insertion into the vessel.

Example 2

Endoprosthetic Device Having Structural Member Encased by Polymer Member

The polymers in Table 2 and the crosslinking agent triallyl isocyanurate are blended and then placed into an extruder. The mixture is further blended in the extruder and then extruded in a cylindrical tube shape. If desired, a rectangular strip can be extruded rather than a cylindrical tube. The tube (or strip) is crosslinked by irradiation with a 2.5 Mrad electron beam.

TABLE 2

| Material | wt % |
| --- | --- |
| polyoctenylene (VESTENAMER, Hulls Corp.) | 70 |
| polyethylene glycol | 25 |
| triallyl isocyanurate | 5 |

A structural member is prepared from Nitinol, available from Shape Memory Applications (Santa Clara, Calif.). A structural member is cut from a flat sheet of the material to the desired geometry.

The endoprosthetic device is prepared by winding the polymer member and the structural member around the balloon section of a balloon catheter. The device is set in place on the catheter by heating the device above the transition temperature of each member, restraining the device in position with a snug-fitting tube and cooling the device to room temperature. The tube is removed prior to inserting the device into the vessel.

Example 3

Device Including Radio-Opaque Members

A. Preparation of Radio-Opaque Film

A radio-opaque polymer film was prepared from the materials listed in Table 3.

TABLE 3

| Material | wt % |
| --- | --- |
| polyethyleneglycol (750) methacrylate (NOF Corp.) | 35 |
| methylmethacrylate (Aldrich) | 35 |
| butyl methacrylate (Rhom Tech Inc) | 24 |
| methacrylic acid | 5 |
| Darocur 1173 (Ciba-Geigy) or AIBN | 1 |

The materials were mixed together in the specified amounts, purged with nitrogen and filtered.

Spherical gold powder having a particle size of between about 1.5-3 μm (Leico Industries, N.Y, N.Y.) and heparin sodium (Sigma Chemical Co., St. Louis, Mo.) were blended in a 9:1 (gold/heparin) ratio and dispersed in the monomer mixture at a gold/heparin/monomer weight ratio of 50/5/45.

The mixture was polymerized between glass plates to form a film having a thickness of approximately 0.09 mm. The polymer film was cut into strips 2 mm wide.

B. Preparation of Polymer Member

A polymer member was prepared as described above in Example 1A, except the radio-opaque strips are placed in the mold prior to pouring the monomer mixture into the mold.

C. Device Preparation

An endoprosthetic device was prepared using the polymer member having radio-opaque members and a low profile stent from Arterial Vascular Engineering (Santa Clara, Calif.) as the structural member. The polymer member was heated above its transition temperature and wrapped around the structural member and cooled while restraining the polymer member in place.

D. X-Ray Opacity

The optical density of the endoprosthetic device prepared in Example 3C was compared to the optical density of the structural member alone, e.g., the stent from Arterial Vascular Engineering. The device and the stent were studied under x-ray fluoroscopy using a copper phantom to imitate the average x-ray optical density of the human body.

The optical density of the endoprosthetic device of Example 3C was determined with the device in its small-diameter, contracted state and in its expanded state after deployment in a polyurethane tubing. The optical density of the structural member was determined in its as-received, small-diameter state and after depolyment in a polyurethane tubing. It was found that the image of the endoprosthetic device of Example 3C was significantly brighter than that of the structural member alone. To quantify the differences, the image was digitally captured and quantified using Adobe Photoshop. The optical densities, in relative units, were:

| | |
| --- | --- |
| endoprosthetic device (small-diameter state) | 155 |
| endoprosthetic device (expanded state) | 173 |
| structural member (small-diameter state) | 122 |
| structural member (expanded state) | 134 |

Example 4

Device Having Polymer Member Adhesively Secured to Structural Member

An endoprosthetic device is prepared as described in Example 1, except the polymer member is adhesively attached to the structural member as follows.

An adhesive is prepared by adding 3 mg of heparin sodium (Sigma Chemical Co.) to 7 mg buffer. The structural member is coated with the heparin adhesive by dipping the member into the solution. The polymer member is slipped over the coated structural member while the heparin adhesive is wet. The device is covered with a snug-fitting tube and heated to above the polymer member's transition and then cooled to room temperature while being restrained by the tubing. The tubing is removed before deployment.

Example 5

In vitro Release of Ticlopidine from Polymer Member

A polymer film for preparation of a polymer member was prepared from the materials in Table 4.

TABLE 4

| Material | wt % |
| --- | --- |
| methylmethacrylate | 44 |
| butyl methacrylate | 14 |
| polyethyleneglycol (550) methacrylate | 31 |
| 1,4 butanedioldimethacrylate | 5 |
| ticlopidine | 5 |
| benzoin methyl ether | 1 |

The materials were mixed in the specified amounts and homogenized until the ticlopidine was dispersed. The monomers were purged with nitrogen and then polymerized between two glass plates by exposure to ultraviolet light. Unpolymerized monomer was removed by soaking the polymer film in a 6% ticlopidine/alcohol solution. The extracted film was then dried in vacuo at a temperature of between 35°–60° C. for 4–6 hours.

In vitro release of ticlopidine was measured from a piece of the film placed in a buffer solution at 37° C. The cumulative amount of ticlopidine in the water was determined from aliquots removed at regular intervals and analyzed for ticlopidine by UV spectrophotometry at 270 nm. The results are shown in FIG. 7A.

Example 6

In vitro Release of Microencapsulated Ticlopidine from Polymer Member

Microcapsules containing entrapped ticlopidine were prepared by dissolving 1.0 gram of 50/50 polylactide/glycolide (Birmingham Polymers, Birmingham, Ala.) in 5.0 grams of dichloromethane. 1.0 gram of ticlopidine was dispersed into the polymer solution. The ticlopidine-containing polymer solution was added to 20 ml of 5% polyvinyl alcohol and 5% ticlopidine aqueous solution with stirring at 1000 rpm. The solution was heated to 40° C. for 3 hours while stirring. The microcapsules were collected by pressure filtration and dried at 40° C. in a vacuum oven.

A polymer film was prepared as described above in Example 5, except 5% microencapsulated ticlopidine was added in place of the ticlopidine.

In vitro release of ticlopidine was measured as described in Example 5, and the results are shown in FIG. 7B.

Example 7

In vitro Release of Vitamin E from Polymer Member

A polymer film for preparation of a polymer member was prepared from the materials in Table 4 of Example 5 above, expect for the addition of 5 wt % of vitamin E, obtained from Sigma Chemical Co. The materials were mixed in the specified amounts and homogenized until dispersed. The monomer mixture was polymerized between two glass by exposure to ultraviolet light.

Figure 8:
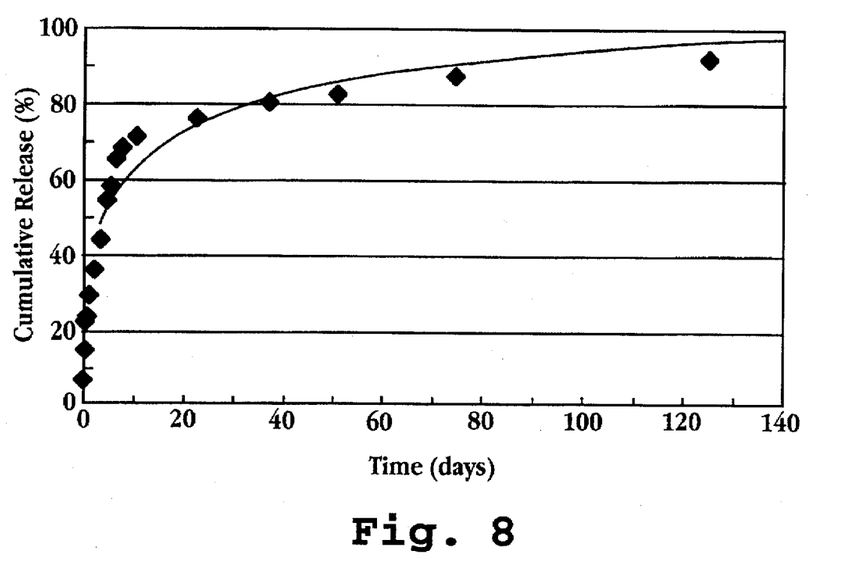
FIG. 8 is a plot showing in vitro cumulative release of vitamin E from a polymer member as a function of time, in days.

In vitro release of vitamin E was measured from a piece of the film placed in an aqueous solution containing 10% ethanol at 37° C. The cumulative amount of vitamin E was determined from aliquots removed at regular intervals analyzed for vitamin E by UV spectrophotometry at 286 nm. The results are shown in FIG. 8.

Example 8

In Vitro Release of Antisense-Oligonucleotide from Polymer Member 0.35 grams of Oxynex K (Roma EM Chem. Co.) was entrapped in 0.65 grams macroporous spherical particles with a mean particle size of 5 μm by stirring the two components until the liquid is absorbed by the particles. 6.2 ml of radio-labelled antisense-oligodeoxynucleotides (Falk Cardiovascular Research Center, Stanford University, Palo Alto, Calif.) solution is added to 35 mg of Oxynex-loaded powder and mixed well.

A polymer member was prepared from the materials in Table 4 (Example 5), expect for the addition of 5 wt % of the antisense-oligodeoxynucleotide/Oxynex-loaded powder.

Figure 9:
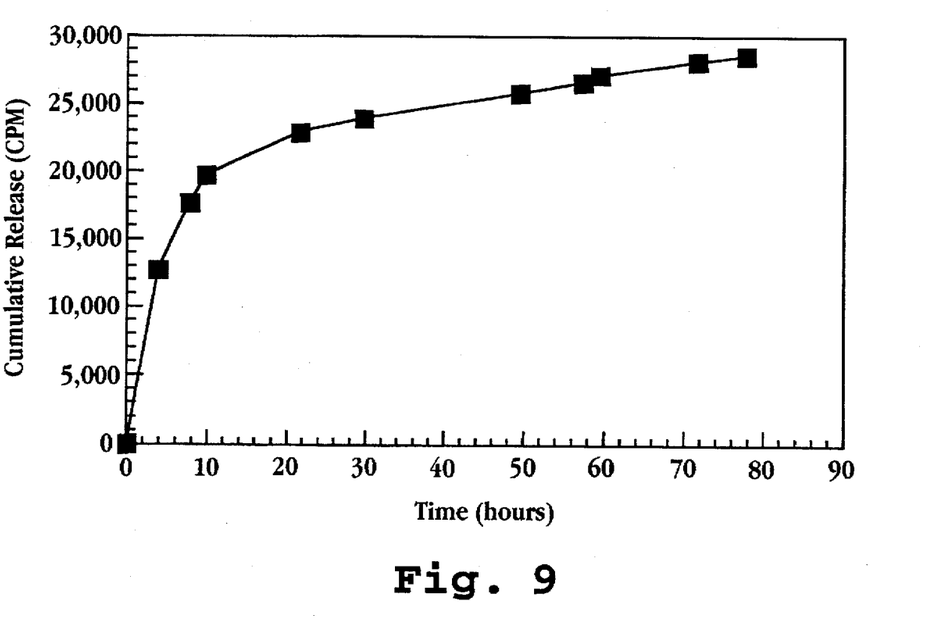
FIG. 9 is a plot showing in vitro cumulative release of antisense oligonucleotide from a polymer member as a function of time, in days.

In vitro release of antisense-oligonucleotide from the polymer member was measured from a piece of the film placed in deionized water at 37° C. The cumulative amount of oligonucleotide was determined from aliquots removed at regular intervals and analyzed by a beta scintillation counter. The results are shown in FIG. 9.

Example 9

In vitro Release of Glutathione from Polymer Member

A polymer film for preparation of a polymer member was prepared from the materials in Table 4 (Example 5) above, expect for the addition of 5 wt % of glutathione obtained from Sigma Chemicals. The materials were mixed in the specified amounts and a polymer film was prepared as described in Example 5.

Figure 10:
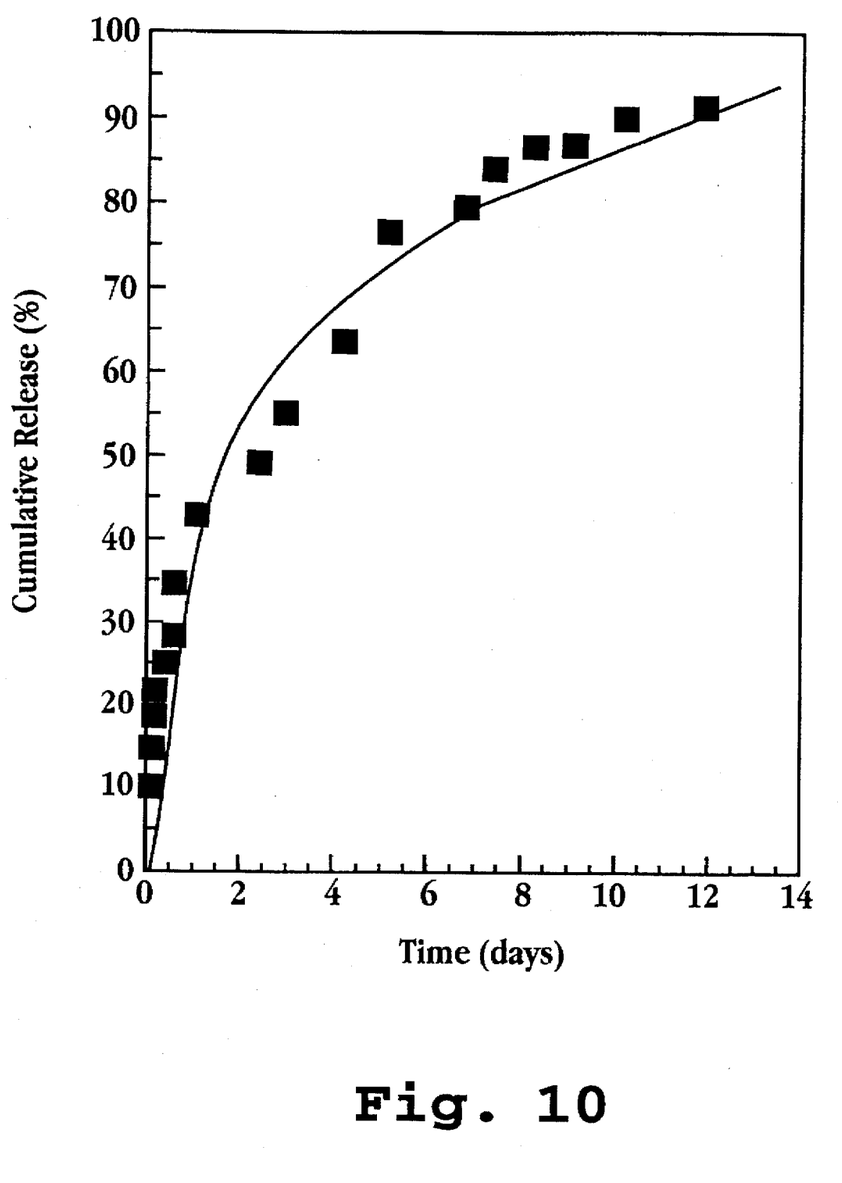
FIG. 10 is a plot showing in vitro cumulative release of glutathione from a polymer member as a function of time, in days.

In vitro release of glutathione was measured from a piece of the film placed in deionized water at 37° C. The cumulative amount of glutathione was determined from aliquots removed at regular intervals and analyzed by UV spectrophotometry at 340 nm, according to the procedure of Tietze (Analytical Biochemistry, 2.7:502–522 (1969). The results are shown in FIG. 10.

Example 10

Polymer Member Containing Heparin In Vitro and In Vivo Release

A polymer member containing neat heparin and entrapped heparin was prepared as follows.

A. Preparation of Entrapped Heparin 3 grams of heparin was dissolved in 7 grams of water. 2 grams of the heparin solution was added to 6 grams of macroporous nanometer-size polymeric particles and mixed until the liquid was absorbed by the polymer particles. The particles are heated in an oven to evaporate the entrapped water and collected after drying.

B. Preparation of Polymer Member

A polymer film was prepared from the materials in Table 5.

TABLE 5

| Material | wt % |
| --- | --- |
| polyethyleneglycol (550) methacrylate | 39 |
| methylmethacrylate | 28 |
| butyl methacrylate | 12 |
| 1,6-hexanedioldimethacrylate (Aldrich) | 5 |
| entrapped heparin | 10.0 |
| neat heparin | 5.0 |
| Darocur 1173 OR AIBN | 1 |

The materials in Table 5 were mixed in the specified amounts and homogenized under a nitrogen-purge until well dispersed. A polymer film and a polymer member were prepared as described in Example 1A.

C. In Vitro Release

Figure 11A:
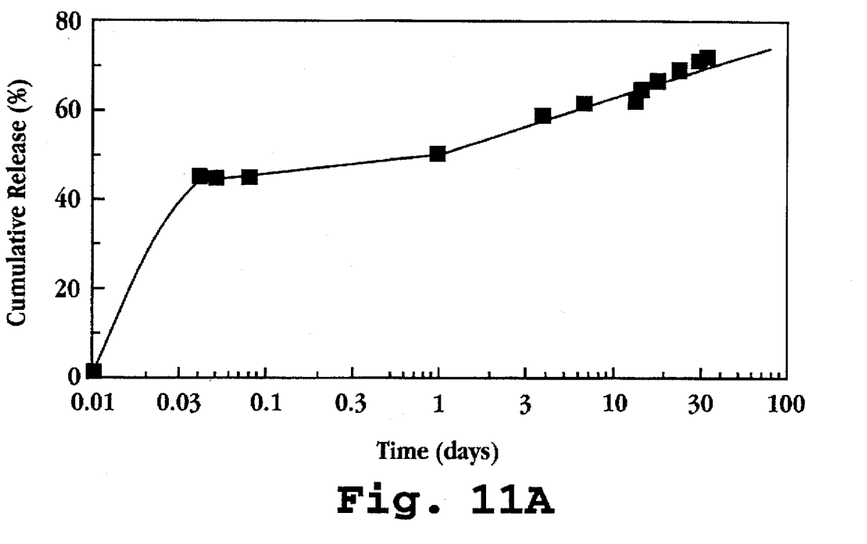
FIGS. 11A–11B are plots showing in vitro (FIG. 11A) and in vivo (FIG. 11B) cumulative release of heparin from a polymer member as a function of time, in days.

Cumulative release of heparin from the polymer member was measured by a colorimetric method at 625 nm (Jacques, L. B. et al., Can. J. Physiol. Pharmacol., 45:787 (1967)) in deionized water at 37° C. The results are shown in FIG. 11A.

D. In Vivo Release

Figure 11B:
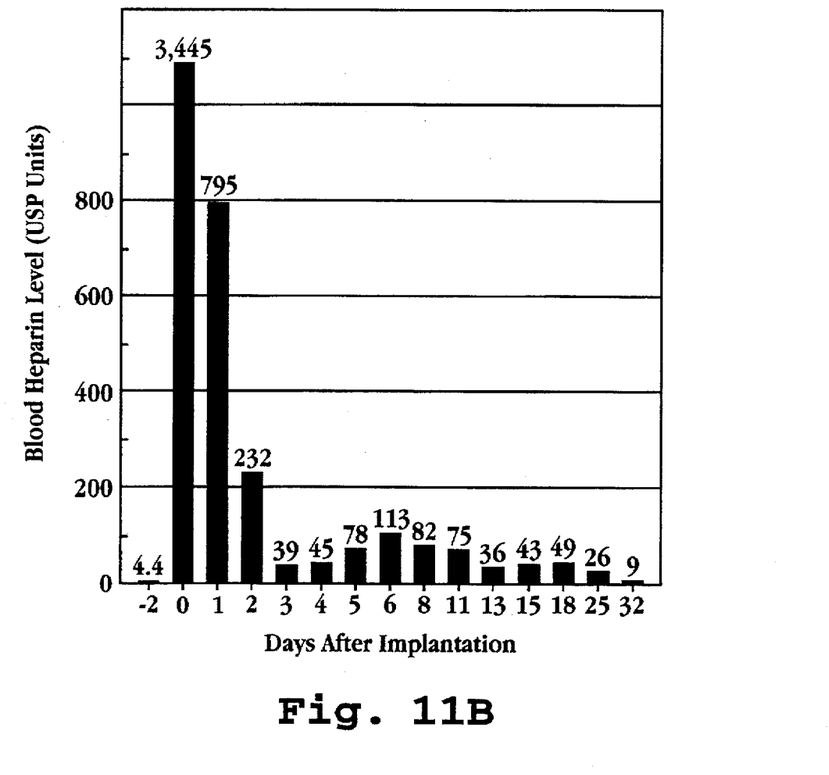

The polymer member was deployed using a modified balloon catheter into a coronary of a young hound. Prior to implantation, a blood sample was taken to determine the baseline heparin blood level of the animal. After implantation, blood samples were taken at regular intervals and analyzed for heparin content. The results are shown in FIG. 11B, and as seen, heparin was released from the polymer member for about 32 days.

From the foregoing, it can be appreciated how various features and objects of the invention are met. The endoprosthetic device of the invention provides a stent for insertion at a vessel target site and for administration of a therapeutic compound. The device is composed of a structural member and of a polymer member, where the compound is embedded in the polymer member. The polymer member of the device provides a large reservoir for loading the therapeutic compound and is composed of a shape-memory polymer. The polymer member can serve as the restraining member for the structural member, to achieve a low profile device. The structural member coexpands with the polymer member for easy deployment at the target site.

Although the invention has been described with respect to particular embodiments, it will be apparent to those skilled in the art that various changes and modifications can be made without departing from the invention.

It is claimed:

1. A drug-delivery endoprosthetic device for insertion at a vascular site via catheter placement at the site, comprising:

a shape-memory polymer member capable of expanding from a contracted substantially cylindrical state to a stable, radially expanded state when the polymer member is exposed to a selected stimulus, said member having a drug embedded therein for release from the member, with such in its expanded state, a structural member on which the polymer member is carried, for coexpansion with the polymer member from a substantially cylindrical state to a radially expanded, cylindrical state when the device is exposed to said stimulus, where the device can be delivered from a catheter, with the structural and polymer members in their contracted states, and is adapted to be held in a vessel at the vascular target site by radial pressure against the wall of the vessel, with the structural and polymer members in their expanded states.

2. The device of claim 1, wherein said polymer member is composed of a shape-memory polymer responsive to a thermal stimulus at a temperature between about 25°–100° C.

3. The device of claim 2, wherein said polymer member is coextensive with said structural member.

4. The device of claim 2, wherein said polymer member encases said structural member and, in its contracted state, is effective to restrain said structural member in its contracted state.

5. The device of claim 2, wherein said thermally-responsive polymer member is formed of a memory polymer having a thermally-activated polymer-state transition selected from the group consisting of:

(a) a melting point of the polymer;

(b) a glass-transition of the polymer;

(c) a liquid crystal transition; and (d) a local mode molecular transition.

6. The device of claim 5, wherein said polymer member is an acrylate-containing or a methacrylate-containing polymer.

7. The device of claim 2, wherein said structural member is responsive to a stimulus selected from the group consisting of heat and radial force.

8. The device of claim 7, wherein said structural member is a metal or alloy selected from the group consisting of Nitinol, stainless steel, titanium, tantalum, cobalt, platinum, and iridium.

9. The device of claim 7, wherein said structural member is composed of a shape-memory alloy for radial expansion at a critical temperature by activating a heat-recoverable memory diameter and said device is heated to said critical temperature.

10. The device of claim 7, wherein said structural member is composed of a heat-activated, shape memory polymer.

11. The device of claim 2, wherein said structural member is composed of a metal and designed for self-expansion.

12. The device of claim 1, wherein said drug is selected from the group consisting of an anticoagulant, an antiproliferative agent, a vasodilator, a nitrate, an antioxidant, antisense oligonucleotide, an antiplatlet agent, and a clot dissolving enzyme.

13. The device of claim 12, wherein said anticoagulant is heparin.

14. The device of claim 1, wherein said polymer member is carried on said structural member by attaching said polymer member to said structural member by an adhesive.

15. The device of claim 14, wherein said adhesive is a biopolymer selected from the group consisting of proteins and peptides.

16. The device of claim 14, wherein said adhesive is prepared from a synthetic polymer which swells or dissolves in water.

17. The device of claim 14, wherein said adhesive is heparin.

* * * * *